US011058969B2

(12) United States Patent
Hudson, III et al.

(10) Patent No.: US 11,058,969 B2
(45) Date of Patent: Jul. 13, 2021

(54) SYSTEM FOR REMOVING THERMAL DEGRADATION PRODUCTS FROM HEAT TRANSFER FLUIDS

(71) Applicants: James G Hudson, III, Salisbury, NC (US); Jay M Railey, Southport, NC (US)

(72) Inventors: James G Hudson, III, Salisbury, NC (US); Jay M Railey, Southport, NC (US)

(*) Notice: Subject to any disclaimer, the term of this patent is extended or adjusted under 35 U.S.C. 154(b) by 0 days.

(21) Appl. No.: 16/275,706

(22) Filed: Feb. 14, 2019

(65) Prior Publication Data

US 2019/0247768 A1    Aug. 15, 2019

Related U.S. Application Data

(60) Provisional application No. 62/630,878, filed on Feb. 15, 2018.

(51) Int. Cl.
| | |
|---|---|
| *B01D 5/00* | (2006.01) |
| *F24S 40/46* | (2018.01) |
| *B01D 1/06* | (2006.01) |
| *F03G 6/00* | (2006.01) |
| *B01D 1/00* | (2006.01) |
| *B01D 1/22* | (2006.01) |

(52) U.S. Cl.
CPC ......... *B01D 5/0063* (2013.01); *B01D 1/0035* (2013.01); *B01D 1/0082* (2013.01); *B01D 1/06* (2013.01); *B01D 1/225* (2013.01); *B01D 5/0003* (2013.01); *B01D 5/006* (2013.01); *B01D 5/009* (2013.01); *B01D 5/0027* (2013.01); *B01D 5/0054* (2013.01); *B01D 5/0075* (2013.01); *F03G 6/003* (2013.01); *F24S 40/46* (2018.05)

(58) Field of Classification Search
None
See application file for complete search history.

(56) References Cited

U.S. PATENT DOCUMENTS 9,211,484 B2 * 12/2015 Martin Sanchez .... C10G 7/006

FOREIGN PATENT DOCUMENTS

WO    WO2018/211467    *  5/2018  ............. C10G 31/00

* cited by examiner

*Primary Examiner* — Derek N Mueller
(74) *Attorney, Agent, or Firm* — Carla Gannon Law (57) ABSTRACT

A system and method removes thermal decomposition components from biphenol and/or diphenyl oxide heat-transfer fluids. Light, volatile decomposition components including benzene, water, hydrogen and phenol leave the system for vapor recovery, chemical adsorption or thermal decomposition. Dimerized and polymerized heavy components such as biphenyl phenyl ether, terphenyl and related isomers are concentrated and recovered. The system can be a continuous, semi-continuous or batch operation. Solar electric plants employing the system can use solar field fluids and heating to operate the system during generator operation hours. A wash system operating at or near atmospheric pressure concentrates heavy thermal decomposition components while allowing removal of light, volatile decomposition components for separation from the majority of the thermal fluid components. Temperature-controlled condensation of the majority of the thermal fluid components allows collection of the thermal fluid, while allowing light, volatile decomposition components to be removed prior to vent processing.

8 Claims, 6 Drawing Sheets

SYSTEM FOR REMOVING THERMAL DEGRADATION PRODUCTS FROM HEAT TRANSFER FLUIDS

CROSS-REFERENCE TO RELATED APPLICATION

This application claims the benefit of U.S. Provisional Patent Application 62/630,878 entitled SYSTEM AND METHOD OF REMOVING THERMAL DEGRADATION PRODUCTS FROM HEAT TRANSFER FLUIDS, filed on Feb. 15, 2018. This provisional application is incorporated by reference in its entirety.

BACKGROUND OF THE INVENTION

The present invention generally relates to concentrated solar power plants, and, in particular, to improved ullage systems for increased recovery of heavy thermal degradation components from high temperature heat transfer fluid systems.

Power plants employ a variety of strategies to produce electricity. Many power plants burn fossil fuels to boil water, with the steam from the boiling water spinning large turbines with those large turbines driving generators to produce electricity. Unfortunately, fossil fuels are generally considered to be economically and/or environmentally undesirable. Using coal and other non-renewable fuel sources are likewise deemed undesirable for the same or similar reasons.

Power plants using solar energy are an alternative to conventional power plants. There are two general methods for producing electricity from solar energy: photovoltaic systems and solar-thermal systems.

Photovoltaic systems employ photovoltaic cells in solar panels that directly absorb sunlight and convert the solar radiation into direct current electricity (DC). The DC from the solar panels is converted downstream into alternating current (AC) that is fed into local electrical utilities. From the utilities, the AC travels through transformers, the voltage is boosted, and is fed through transmission lines for distribution to the end users.

Solar-thermal systems use solar collectors that capture and concentrate sunlight to heat a heat-transfer fluid. The heat-transfer fluid heats and boils water to create super-heated steam, and the steam is directed to turbine-generators to produce electricity, which is transmitted over power lines. A supplemental natural gas boiler typically heats water to create steam and therefore, energy on cloudy days.

There are three main types of concentrating systems used in solar-thermal energy production: linear concentrator systems, dish/engine systems, and power tower systems.

Linear concentrator systems collect the sun's energy using long u-shaped mirrors that are articulated to track the sun and focus the sunlight onto solar collector tubes along the length of the mirrors. The tubes contain heat-transfer fluid. The reflected sunlight heats the heat-transfer fluid, which is used to boil water to motivate a conventional steam-turbine generator to produce electricity. There are two major types of linear concentrator systems: parabolic trough systems, where receiver tubes are positioned along the focal line of each parabolic mirror, and linear Fresnel reflector systems, where one receiver tube is positioned above several mirrors to allow the mirrors greater mobility in tracking the sun.

A dish/engine system uses a dish-shaped mirror, or series of mirrors formed into a dish shape, which directs and concentrates sunlight onto a thermal receiver. The thermal receiver absorbs and collects the heat and transfers it to an engine generator. The most common type of heat engine in dish/engine systems is the Stirling engine, wherein heat transfer fluid that has been heated by the receiver moves pistons and creates mechanical power, which runs a generator or alternator to produce electricity.

A power tower system uses a series of large, flat, sun-tracking mirrors to focus and concentrate sunlight onto a receiver positioned on the top of a tower. A heat-transfer fluid, typically molten salt, is heated in the receiver and is used to generate steam, which is used in a conventional turbine generator to produce electricity.

Of the various types and subtypes of concentrating systems used in solar-thermal energy production, the parabolic trough, a version of a linear concentrator system, is particularly promising.

The efficiency of a system correlates with the temperature of the rejection heat transfer fluid in the system. Said another way, the hotter the heat transfer fluid, the higher the efficiency of the operation. Thus, it is advantageous for the heat transfer fluid to reach the higher limit of the operating range. However, the higher in that range the system operates, the greater the rate of thermal degradation in the heat transfer fluid.

Figure 1:
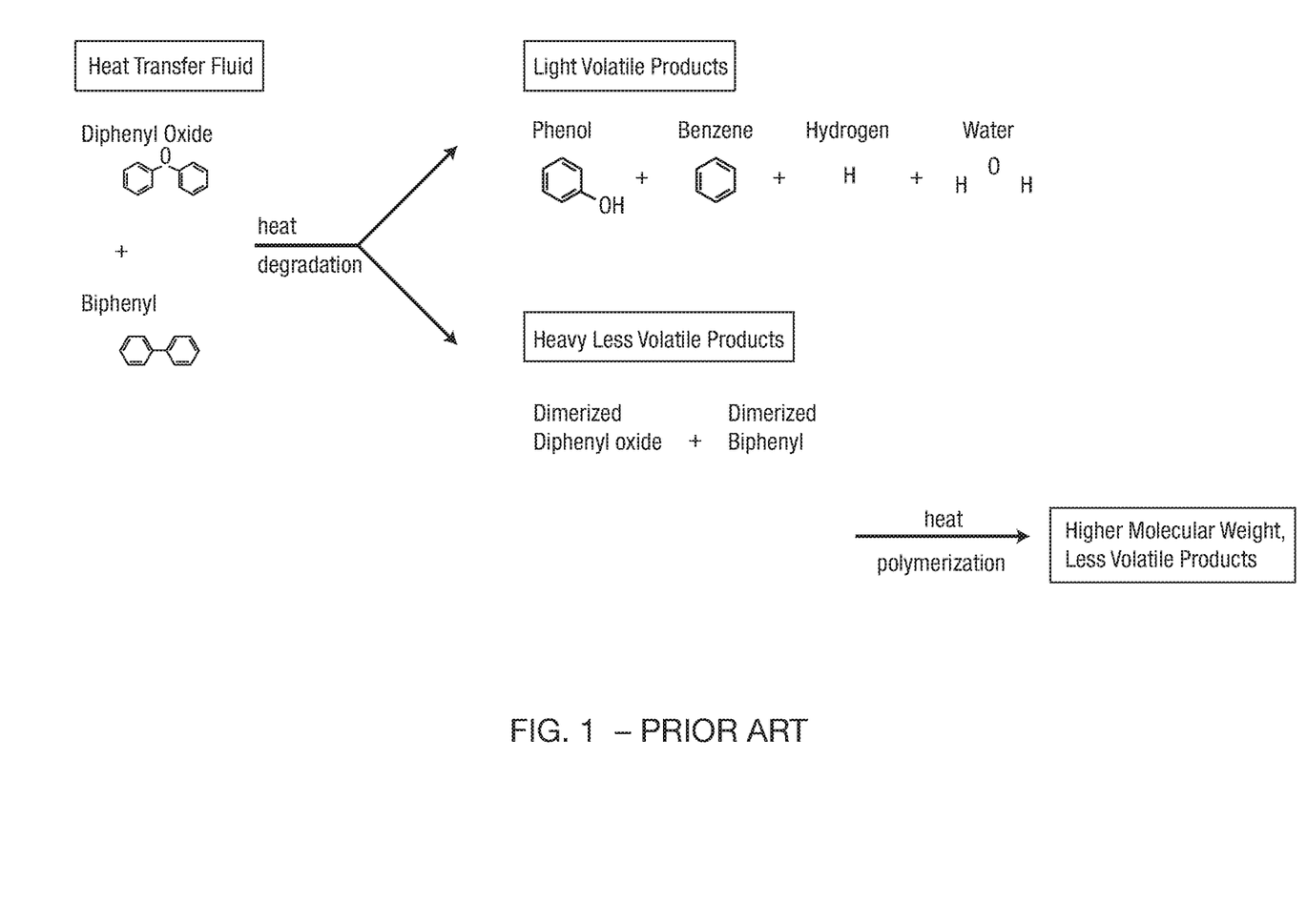
FIG. 1 depicts known thermal degradation of heat transfer fluid.

DOWTHERM-A and THERMINOL-VP-1 are the most commonly used heat transfer fluids, and are both eutectic mixtures of biphenyl and diphenyl oxide. While these fluids are essential to the overall system, they naturally have limitations. For example, the normal operating temperature for a parabolic trough system is above 650° F. and can be as high as 750° F. The upper temperature limit for these fluids is 750° F. The normal boiling point of DOWTHERM-A and THERMINOL-VP-1 is 495° F. As depicted in FIG. 1, heat-transfer fluids follow a fairly predictable thermal degradation profile, and generally break down into "light" components including phenols, benzenes, water and hydrogen, and "heavy" components including diphenyl phenyl ether and others. The breakdown components affect performance of the system in a variety of ways. For example, monoatomic hydrogen, formed during degradation reactions, travels through the inner pipe of the collector tubes and degrades the insulating vacuum between the inner pipe and the glass outer tube, which reduces collection efficiency of the solar collectors. Degradation also affects the heat transfer properties of the fluid and fouling affects in the heat transfer equipment.

Figure 2:
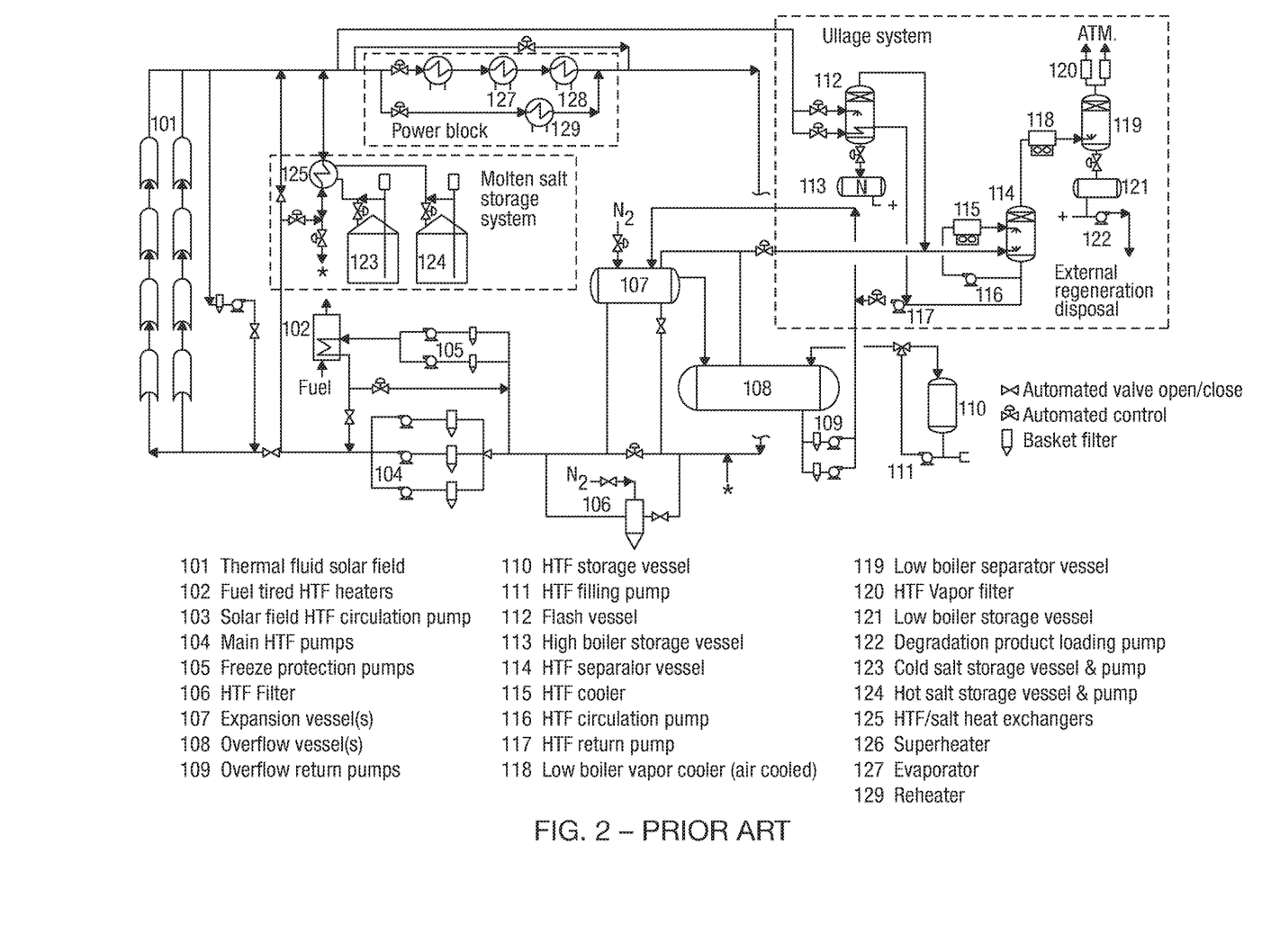
FIG. 2 schematically depicts a known concentrated solar plant, including a known ullage system.

As shown in FIG. 2, a ullage system may be employed for reclamation of thermally degraded heat-transfer fluids. In general, the ullage system is a multiple effect evaporation system that first separates the high molecular weight high boiling species from the heat transfer fluid and light components. A second effect separates the low boiling degradation components from the heat transfer fluid. The high boilers are collected and shipped off of the site as a non-hazardous, non-spec liquid fuel, and the low boilers are condensed and collected for either off-site disposal or can be destroyed on site in a thermal oxidizer. Although a ullage system in connection with a solar plant is discussed herein, it should be understood that the inventions described herein can be used with industrial plants that employ ullage systems. Examples of industrial plants include plants that produce ethylene oxide, glycol, fibers, and polymer processing.

HTF Cooler 115 removes heat to separator vessel 114 to condense collected heat transfer fluid. Unfortunately, this design also condenses a large portion of the phenol in the light decomposition products. This design feature contaminates the purified heat transfer fluid being returned to the heat transfer system.

The vapor exiting separator vessel 114 passes through a low boiler vapor cooler (air cooled) where a portion of the remaining light decomposition products are condensed. Low boiler separator vessel 119 collects condensed material for external regeneration disposal 122, while the vapor is discharged to atmosphere. This is current art and unfortunately, these systems condense degradation products into the recovered heat transfer fluid.

In theory, the collected ullage material should contain a minimum of 50% heat transfer fluid. This collected residue is reprocessed off-site by third party processors. The collected heat transfer fluid from this reprocessing is then returned to the heat transfer system. Unfortunately, however, this existing design doesn't actually accomplish what it is intended to do.

As can be seen, there is a need for an improved system for separating thermal decomposition components from heat transfer fluids. It is desirable that this system is economical and environmentally advantageous. It is also desirable that this system can reduce the level of "heavy" components to ≤1% by weight of circulating heat-transfer fluid. It is also desirable that this system can remove the "light" components. It is also desirable that this system can reduce the reprocessing expense of ullage residue. It is also desirable that the system be simple in its operation and require minimal operator interaction after start-up. A new system design can also provide effective separation of the light components from the recovered heat transfer fluid.

SUMMARY OF THE INVENTION

The present invention addresses the problems identified above by providing a system and method for effectively removing significant amounts of thermal decomposition material from ullage system feedstock. These decomposition products are concentrated and clarified to facilitate disposal as a light, volatile vapor or a concentrated heavy component residue.

The present invention includes a wash column with reflux to concentrate ullage residue and promote easy collection of ullage vapor waste material. Rectification and washing of the vaporized heat transfer fluid mixture forces the heavy components into the ullage residue while allowing the light components to pass overhead to tempered condensation and collection.

Heat for the wash column is provided by an evaporator. Either a forced circulation evaporator, thin film evaporator or wiped film evaporator may be used to concentrate ullage residue in the wash column. The wash column operates at or slightly above atmospheric pressure. Because of boiling point rise effects, the wash column operates above the boiling point temperature of the heat transfer fluid at column operating pressure.

Condensing of the wash column overhead material preferably occurs at a sufficiently high temperature to prevent condensation of light thermal decomposition components. This is accomplished by a tempering condenser. This condenser may be either a heat exchanger with tempering fluid as the heat transfer medium or a direct-contact condenser using the bulk heat transfer fluid as the condensing medium.

A reboiled collection vessel collects the bulk heat transfer fluid while vaporizing the light thermal decomposition components overhead. A portion of the collected bulk heat transfer fluid is returned to the wash column as reflux.

The overhead vapor is condensed by either cooling water or air before the vapors are transported to vent collection.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The following structure numbers shall apply to the following structures among the various FIGS.:
- 10—recovery system;
- 20—ullage system feed;
- 22—flash vessel;
- 24—wash column;
- 26—reflux;
- 28—overhead vapor;
- 30—first reboiler;
- 31—wash column residue;
- 32—circulation pump;
- 33—small transfer pump;
- 34—residue fluid;
- 36—forced circulation reboiler feed;
- 38—heat transfer fluid;
- 40—heat exchanger;
- 42—tempering medium;
- 44—condensate;
- 50—second reboiler;
- 52—cooling water;
- 54—purified heat transfer fluid;
- 60—collection vessel;
- 62—direct contact condenser;
- 63—direct-contact condenser circulation fluid;
- 64—air-cooler/heat exchanger;
- 66—thermosyphon reboiler circulation fluid-clean fluid;
- 68—decomposition material;
- 70—final condenser; and
- 72—vent discharge material.

Broadly, the present invention pertains to a system for separating thermal decomposition components from heat transfer fluids, and, more particularly, to improving performance of solar thermal fluid power plants and reducing their maintenance costs.

Figure 3:
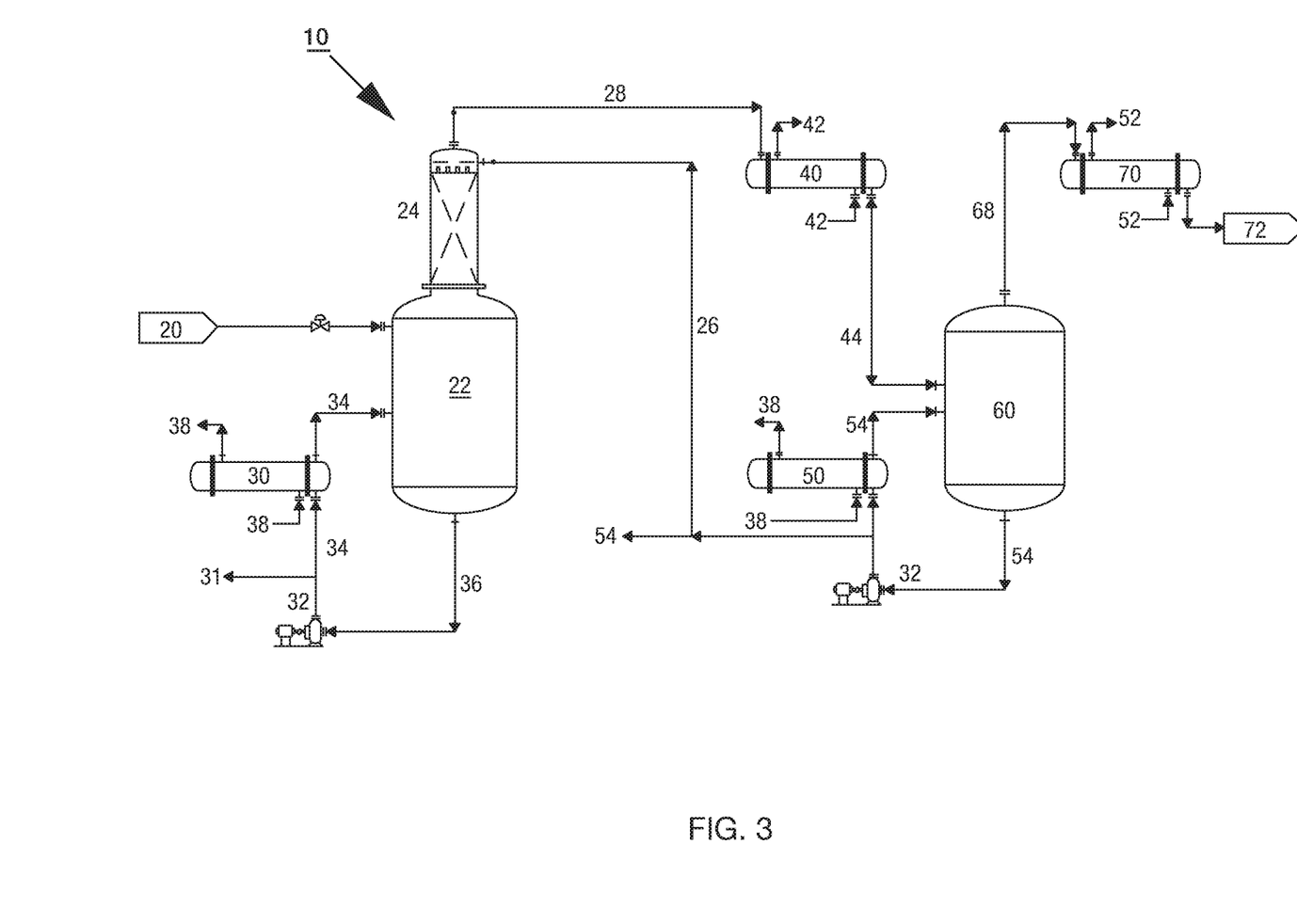
FIG. 3 is schematic representation of a tempered condenser recovery system with tempering fluid as the condensing medium, according to an embodiment of the invention.

FIG. 3 illustrates a preferred embodiment of the system of the present invention, basically including a rectified wash column 24 with forced-circulation reboiler 30 processing ullage material from the high temperature heat transfer system. The reboiler may be forced circulation, thin film evaporator or wiped film evaporator. The concentration of heavy thermal decomposition components in the ullage system feed 20 is above 2% by weight. The concentration of heavy thermal decomposition components in the residue 31 from the combination flash vessel 22/wash column 24 is greater than, or equal to 50% by weight. Heating for the reboiler 30 is sensible heating only due to fouling of the heavy thermal decomposition components on the first reboiler 30. Heating of the residue fluid 34 is only 8-12 Deg. F, while insuring that no vaporization of the fluid 34 occurs in the first reboiler 30. Heating for the reboiler 30 is provided by either a higher temperature heat source or by the ullage system feed 20. Circulation on the reboiler 30 is set by circulation pump 32 to maintain sensible heating in the reboiler 30.

The overhead vapor 28 from the wash column 24 is slightly above atmospheric pressure at a temperature close to the saturation temperature of the purified heat transfer fluid 54. Sufficient material is vaporized in the wash column 24 to provide wash fluid reflux 26 to the wash column and concentrate the heavy thermal decomposition components into the wash column residue 31.

The overhead vapor 28 is condensing in a tempering condenser heat exchanger 40 with tempering medium 42 sufficient to not sub-cool the condensate 44 from saturated liquid status and limiting condensation of some of the light thermal decomposition components. Condensed, two-phase fluid 44 exits the tempering condenser 40 and is piped into a collection vessel 60. A reboiler 50 on the collection vessel 60 maintains the temperature in the collection vessel to force light decomposition material 68 to be vaporized and pass overhead into a final condenser 70. The reboiler 50 on FIG. 3 is a forced-circulation second reboiler 50 sensibly heating the purified heat transfer fluid 54 only 8 to 12 Deg. F, while ensuring that no vaporization of the fluid 54 occurs. Circulation on the reboiler 50 is set by circulation pump 32 to maintain sensible heating on the reboiler 50.

Material from the final condenser 70 has been cooled with cooling water 52 (or air) to produce vent discharge material 72. Stream of vent discharge material 72 is piped into a vent collection charge tank for vapor/liquid separation and further processing.

Material contained in the collection vessel 60 is sufficiently purified to return to the heat transfer system. A portion of the purified heat transfer fluid 54 is metered back to the wash column 24 as reflux 26.

It is important to understand that condensation of the overhead vapor 28 must be temperature-controlled and tempered to prevent condensation of the light thermal decomposition components. This can be accomplished by a shell and tube condenser with a tempering fluid 42. Bulk heat transfer fluid is collected in collection vessel 60.

Figure 4:
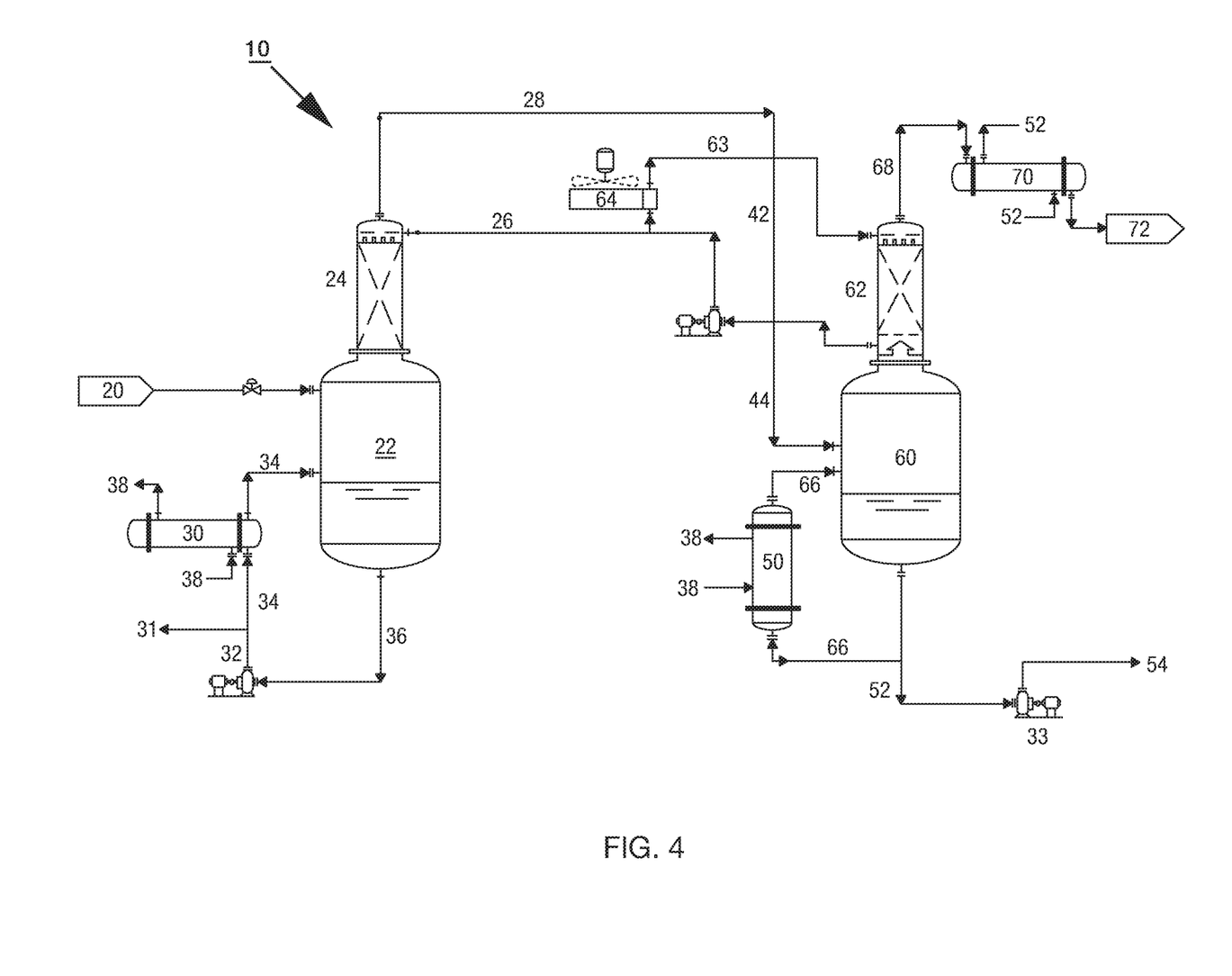
FIG. 4 is schematic representation of a direct-contact condenser recovery system with collected heat transfer fluid as the condensing medium, according to an embodiment of the invention.

FIG. 4 illustrates another preferred embodiment of the system of the present invention incorporating a direct-contact condenser 62 into the design of the heat transfer fluid collection vessel 60.

The overhead vapor 28 exiting the wash column is condensed by using the bulk heat transfer fluid as the condensing media 63. Temperature is controlled by an external heat exchanger 64 sensibly cooling the heat transfer fluid slightly to force light thermal decomposition products 68 into the overhead of collection vessel 60 while condensing the bulk heat transfer fluid. This heat exchanger is shown as an air-cooler 64, but can be a conventional shell and tube exchanger with suitable tempering medium.

The direct-contact condenser 62 can be either installed in the top of the collection vessel 60 or in a separate vessel processing collection vessel 60 overhead product.

The reboiler 50 in FIG. 4 shows a vertical thermosyphon design. Because a clean fluid 66 is being processed at atmospheric pressure, a forced circulation pump is not required. Vaporization in the reboiler 50 provides the driving force for circulation. With this reboiler design, a small transfer pump 33 is required to return clean product to the heat transfer system.

This ullage system design applies to all large heat transfer systems involving this heat transfer fluid chemistry. Small heat transfer systems holding a few hundred gallons of heat transfer fluid may not economically benefit from using such a ullage system.

Figure 5:
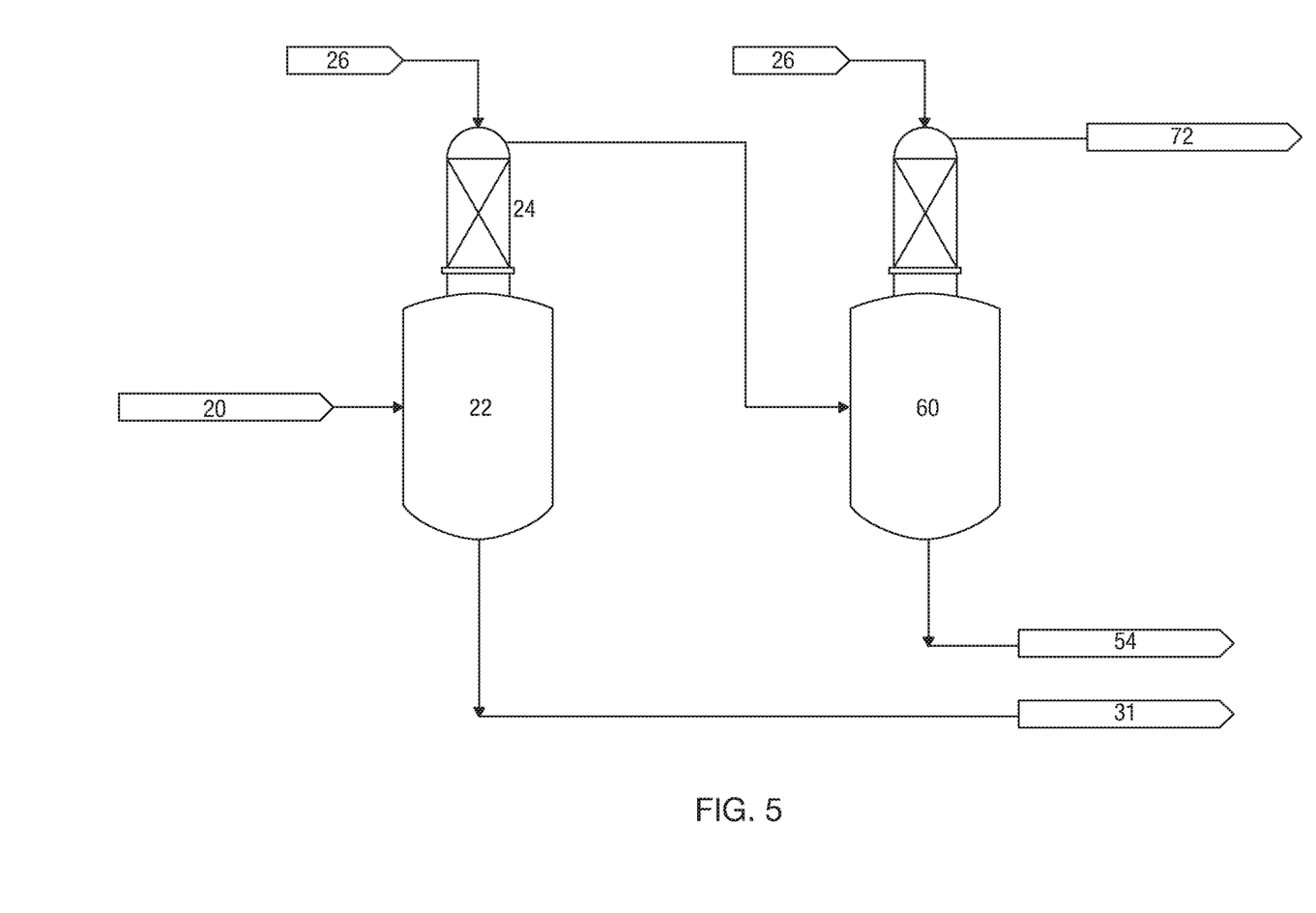
FIG. 5 is a simplified Process Flow Diagram showing fractional splits of the various streams and their constituent concentrations.

FIG. 5 is a basic Process Flow Diagram showing the principal material flow streams generated by the system. The contaminated material from the solar field is fed into the system and split into three separate streams: a high boiler bottoms stream, a low boiler lights stream, and refined BP/DPO which is then returned to the solar field. The 50,000 pounds feed value shown in the material balance is representative of the amount of feed that can be processed in one typical day.

Table 1 sets forth fractional splits of the various streams and their constituent concentrations:

TABLE 1

| | Fractions Splits and Constituent Concentrations | | | | | | | |
|---|---|---|---|---|---|---|---|---|
| | FROM SOLAR FIELD | | H.B. RESIDUE | | VENT COLLECTION | | RETURN TO FIELD | |
| CONSTITUENTS | LB | % | LB | % | LB | % | LB | % |
| BP/DPO | 44500.00 | 89.00 | 2132.14 | 30.00 | 211.84 | 29.864 | 42156.02 | 99.935 |
| HIGH BOILERS | 5000.00 | 10.00 | 4975.00 | 70.00 | 0.00 | 0.000 | 25.00 | 0.059 |
| LOW BOILERS | 500.00 | 1.00 | 0.00 | 0.00 | 497.50 | 70.136 | 2.50 | 0.006 |
| TOTAL | 50000.00 | | 7107.14 | | 709.34 | | 42183.52 | |

Figure 6:
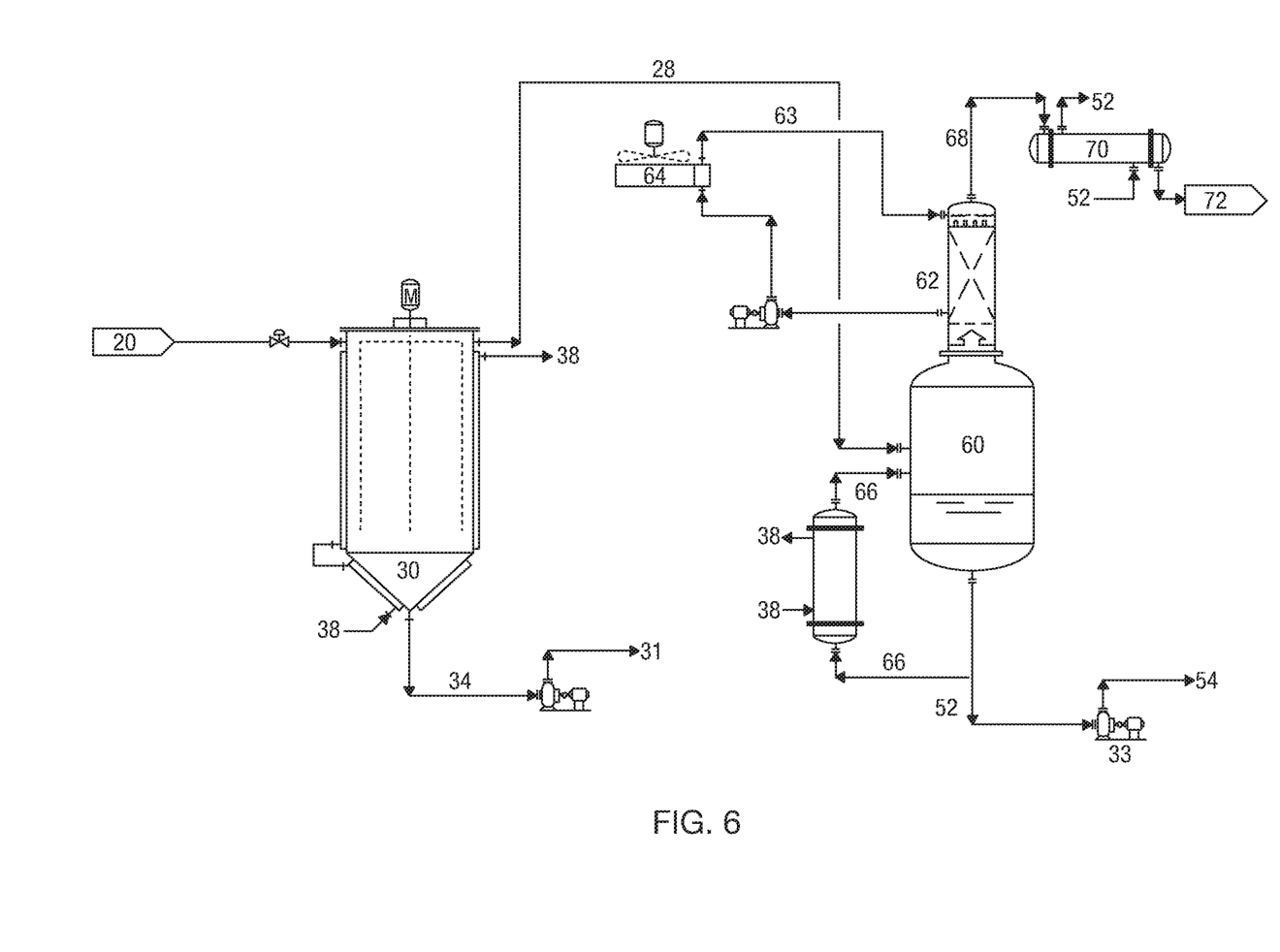
FIG. 6 is a schematic representation of a wiped film evaporator being used as the wash column, with a direct-contact condenser system and collected heat transfer fluid as the condensing medium being used in the collection vessel.

FIG. 6 illustrates another preferred embodiment of the system of the present invention incorporating a thin film or wiped film evaporator 30 in the place of the flash tank 22 and wash column 24.

Heat transfer fluid 38 is used to vaporize light thermal decomposition components 28 and concentrate heavy thermal decomposition components 31.

Volatilized overhead vapor 28 is partially condensed using the bulk heat transfer fluid as direct-contact condenser circulation fluid 63. Temperature is controlled by an external heat exchanger sensibly cooling the heat transfer fluid slightly to force light thermal decomposition material 68 into the overhead of collection vessel 60 while condensing the bulk heat transfer fluid. The heat exchanger is shown as an air-cooler 64, but can be a conventional shell and tube exchanger with suitable tempering medium.

Reboiler 50 in FIG. 6 shows a vertical thermosyphon design. Because clean thermosiphon reboiler circulation fluid 66 is being processed at atmospheric pressure, a forced circulation pump is not required. Vaporization in reboiler 50 provides the driving force for circulation. With this reboiler design, small transfer pump 33 is required to return clean product to the heat transfer system.

Certain structures and components are disclosed for purposes of describing an embodiment, and setting forth the best mode, but should not be construed as teaching the only possible embodiment. Rather, modifications may be made without departing from the spirit and scope of the invention as set forth in the following claims. Examples of modifications include alternate reboiler designs including thin film and wiped film evaporators, and alternate condenser designs including spiral designs, and direct contact equipment. Alternate heating methods can also be considered. It should be understood that all specifications, unless otherwise stated or contrary to common sense, are +/−10%, and that ranges of values set forth inherently include those values, as well as all increments between. Also, "substantially" as used herein, shall mean generally. By way of example a "substantially planar" surface includes surface imperfections but is generally planar.

What is claimed is:

1. An industrial plant including:
   A. A system configured for removing thermal degradation products from heat transfer fluids, said system comprising:
      1. a wash column with reflux, said wash column generating vapor;
      2. a first reboiler for heating said wash column;
      3. a tempering condenser in contact with said vapor, said tempering condenser generating condensate;
      4. a collection vessel in fluid communication with said tempering condenser; and
      5. a second reboiler in fluid communication with said collection vessel, said second reboiler for vaporizing light thermal decomposition components from said condensate;
   B. Heat transfer fluid circulating within said system;
   C. Degradation products within said heat transfer fluid; and
   D. Heavy components within said degradation products, wherein said heavy components include constituents selected from the group consisting of biphenyl phenyl ether, terphenyl, dimerized diphenyl oxide, dimerized biphenyl, isomers thereof and combinations thereof.

2. The industrial plant of claim 1 wherein said heat transfer fluid includes ≤1% by weight of said heavy components.

3. The industrial plant of claim 1 wherein said heat transfer fluid is within approximately 10° F. of the normal boiling point of said heat transfer fluid.

4. The industrial plant of claim 1 wherein said first reboiler is an evaporator, said evaporator providing heat to said wash column.

5. The industrial plant of claim 4 wherein said evaporator is selected from the group consisting of a forced circulation evaporator, thin film evaporator, wiped film evaporator, or combinations thereof.

6. The industrial plant of claim 1 wherein said light thermal decomposition components include constituents selected from the group consisting of phenol, benzene, hydrogen, water and combinations thereof.

7. The industrial plant of claim 1 wherein said tempering condenser is a heat exchanger with a tempering fluid as a heat transfer medium.

8. The industrial plant of claim 1 wherein said tempering condenser is a direct-contact condenser using said heat transfer fluid as a condensing medium.

\* \* \* \* \*